United States Patent
Chan et al.

(10) Patent No.: US 10,197,569 B1
(45) Date of Patent: **\*Feb. 5, 2019**

(54) IN VITRO HOMOGENOUS CELL BLOCK, METHOD OF MAKING AND USING

(71) Applicant: Alamak Biosciences Incorporation Company Limited, Ma On Shr (HK)

(72) Inventors: Pokman Chan, Salem, MA (US); James Wang, Salem, MA (US); Hok-Yu Chan, New Territories (HK)

(73) Assignee: Alamak Biosciences Incorporation Company Limited, Ma On Shan (HK)

( * ) Notice: Subject to any disclaimer, the term of this patent is extended or adjusted under 35 U.S.C. 154(b) by 46 days.

This patent is subject to a terminal disclaimer.

(21) Appl. No.: 15/178,205

(22) Filed: Jun. 9, 2016

Related U.S. Application Data

(62) Division of application No. 13/801,617, filed on Mar. 13, 2013, now Pat. No. 9,395,283.

(60) Provisional application No. 61/610,556, filed on Mar. 14, 2012.

(51) Int. Cl.
*C12Q 1/6841* (2018.01)
*G01N 33/551* (2006.01)

(52) U.S. Cl.
CPC ......... *G01N 33/551* (2013.01); *C12Q 1/6841* (2013.01)

(58) Field of Classification Search
None
See application file for complete search history.

(56) References Cited

U.S. PATENT DOCUMENTS

| 5,457,050 A | 10/1995 | Mazurek |
| 6,913,921 B2 | 7/2005 | Fischer |
| 7,541,161 B2 | 6/2009 | Fischer |

(Continued)

FOREIGN PATENT DOCUMENTS

| EP | 1642131 B1 | 10/2008 |
| WO | WO2004077057 A1 | 9/2004 |

(Continued)

OTHER PUBLICATIONS

ASC—Applied StemCells Genome Editing in Vitro and in Vivo—website URL www.appliedstemcell.com.
Office Action dated Sep. 28, 2015 in connection with U.S. Appl. No. 13/801,617.
Office Action dated Mar. 21, 2016 in connection with U.S. Appl. No. 13/801,617.

(Continued)

*Primary Examiner* — Suchira Pande
(74) *Attorney, Agent, or Firm* — Carrie Stroup

(57) ABSTRACT

An in vitro experimental standard comprising sections cut from a homogenous cell block for use as a positive control for biomarkers in immunohistochemistry experiments. The homogenous cell block is produced using a three layered vertical apparatus to create an evenly distributed suspension of FFPE cells, wherein the cells are mixed with 3% agarose while still rotating within the apparatus's middle layer. The injection of the cell mixture into a mold creates a homogeneous cell block where each cell, or ratio of different types of cells, is evenly distributed. The cell mixture within the cell block may further comprise: a mixture of the same type of cell with different genetic modifications; a mixture of the same type of cell with different protein or nucleic acids expression; and a mixture of different types of cells with different genetic backgrounds, and/or different expression level of genes and/or proteins.

10 Claims, 6 Drawing Sheets

(56) References Cited

U.S. PATENT DOCUMENTS

| | | | |
|---|---|---|---|
| 9,097,618 | B2 | 8/2015 | Barker et al. |
| 9,395,283 | B1 | 7/2016 | Chan et al. |
| 9,909,964 | B2 | 3/2018 | Boonyaratanakornkit et al. |
| 2003/0157523 | A1* | 8/2003 | Frantz .................. G01N 1/36 506/23 |
| 2006/0154234 | A1 | 7/2006 | Winther et al. |
| 2007/0037138 | A1 | 2/2007 | Winther |
| 2007/0218542 | A1 | 9/2007 | Li |
| 2008/0082351 | A1 | 4/2008 | Kelley-Hrabe et al. |
| 2011/0306064 | A1 | 12/2011 | Taylor et al. |
| 2012/0088233 | A1 | 4/2012 | Boonyaratanakornkit et al. |
| 2013/0183710 | A1 | 7/2013 | Reifenberger et al. |
| 2014/0335533 | A1 | 11/2014 | Boonyaratanakornkit et al. |

FOREIGN PATENT DOCUMENTS

| | | |
|---|---|---|
| WO | WO2005003773 A1 | 1/2005 |
| WO | WO2012051332 A1 | 4/2012 |
| WO | WO2016010858 A1 | 1/2016 |

OTHER PUBLICATIONS

Koch et al., "Real-time Quantitative RT-PCR Shows Variable, Assay-dependent Sensitivity to Formalin Fixation: Implications for Direct Comparison of Transcript Levels in Paraffin-embedded Tissues", Diagn Mol Pathol. (2006) vol. 15:149-156.

Shi et al., "DNA Extraction from Archival Formalin-fixed, Paraffin-embedded Tissue Section Based on the Antigen Retrieval Principle: Heating Under the Influence of pH", J. Histochem Cytochem. (2002) vol. 50: 1005-1011.

U.S. Appl. No. 13/801,617 of Chan, P. filed Mar. 13, 2013.

U.S. Appl. No. 15/186,536 of Chan, P. filed Jun. 19, 2016.

U.S. Appl. No. 15/178,103 of Chan, P. filed Jun. 9, 2016.

Office Action dated Dec. 26, 2017 in connection with U.S. Appl. No. 15/178,103.

Office Action dated Jan. 2, 2018 in connection with U.S. Appl. No. 15/186,536.

Alamak Biosciences, slide presentation entitled "Seeing is Believing Seeing is Deceiving Towards a Standardization of Histology in Biomarker Qualification".

* cited by examiner

Cell block paraffin processing schedule

| Medium | Time | Temperature |
|---|---|---|
| 70% EtOH | 2 Hours | RT |
| 70% EtOH | 2 Hours | RT |
| 70% EtOH | 2 Hours | RT |
| 80% EtOH | 2 Hours | RT |
| 80% EtOH | 2 Hours | RT |
| 95% EtOH | 2 Hours | RT |
| 95% EtOH | 2 Hours | RT |
| 100% EtOH | 2 Hours | RT |
| 100% EtOH | 2 Hours | RT |
| 100% EtOH | 2 Hours | RT |
| Slide Brite | 2 Hours | RT |
| Slide Brite | 2 Hours | RT |
| Slide Brite | 2 Hours | RT |
| Paraffin | 2 Hours | 56°C Oven |
| Paraffin | 2 Hours | 56°C Oven |
| Paraffin | 2 Hours | 56°C Oven |

FIG. 3

| Solution | Time |
|---|---|
| Xylene | 5 Minutes |
| Xylene | 5 Minutes |
| Xylene | 5 Minutes |
| 100% EtOH | 5 Minutes |
| 100% EtOH | 5 Minutes |
| 100% EtOH | 5 Minutes |
| 95% EtOH | 5 Minutes |
| 95% EtOH | 5 Minutes |
| 80% EtOH | 5 Minutes |
| 80% EtOH | 5 Minutes |
| 70% EtOH | 5 Minutes |
| 70% EtOH | 5 Minutes |
| ddH2O | 5 Minutes |
| ddH2O | 5 Minutes |
| Hematoxylin | 30 Seconds |
| Running Tap Water | 5 Minutes |
| Scott's Bluing Solution | 30 Seconds |
| Running Tap Water | 5 Minutes |
| ddH2O | 5 Minutes |
| 70% EtOH | 5 Minutes |
| 70% EtOH | 5 Minutes |
| 80% EtOH | 5 Minutes |
| 80% EtOH | 5 Minutes |
| 95% EtOH | 5 Minutes |
| 95% EtOH | 5 Minutes |
| 100% EtOH | 5 Minutes |
| 100% EtOH | 5 Minutes |
| Xylene | 5 Minutes |
| Xylene | 5 Minutes |

FIG 4

In Vitro Tissue: Precision Homogenous Cell Block Assay

| Cell Block Initial Number of Cells | Cell Number per 10 micrometer Section (1200 Sections Total) | DNA Yield per 10 micrometer Section |
|---|---|---|
| 20 million | 11,650 | 62 |
| 40 million | 23,889 | 131 |
| 80 million | 61,170 | 245 |
| 160 million | 126,500 | 512 |

FIG. 5

IN VITRO HOMOGENOUS CELL BLOCK, METHOD OF MAKING AND USING

CROSS-REFERENCE TO RELATED APPLICATIONS

This application is a divisional application of U.S. application Ser. No. 13/801,617, filed on Mar. 13, 2013, that issued as U.S. Pat. No. 9,395,283, which claims the benefit of Provisional U.S. Patent Application Ser. No. 61/610,556 filed Mar. 14, 2012, the contents of both of which are incorporated herein by reference in their entirety.

FIELD OF THE INVENTION

The present invention pertains to methods for embedding cellular materials within a formalin fixed paraffin substrate to create a cell block of evenly distributed cell densities for use as a standard in immunohistochemistry experiments.

BACKGROUND OF THE INVENTION

Immunohistochemistry (IHC) and in situ hybridization (ISH) are in vitro laboratory procedures used to detect and diagnose abnormal conditions, such as cancer. IHC requires detecting proteins in cells of a tissue section by hybridizing antibodies to antigens, while ISH hybridizes radiolabelled complementary DNA/RNA probe to DNA/RNA within a tissue. The procedures are also widely used in basic research to understand the distribution and localization of biomarkers and differentially expressed proteins/DNA in different parts of a biological tissue.

According to the FDA Draft "Guidance for Industry Use of Histology in Biomarker Qualification Studies", released December 2011, a biomarker is defined as: "a characteristic that is objectively measured and evaluated as an indicator of normal biologic processes, pathogenic processes, or biological responses to a therapeutic intervention". The report goes on to state that a poorly characterized biomarker can do considerable harm. A poorly characterized biomarker may lead to inappropriate removal of a drug from development, encourage development of a drug that is unlikely to be approved, or lead to an erroneous perception of safety.

Positive and negative experimental controls for IHC and ISH are created from archived tissue blocks, or from cell lines embedded in tissue medium (i.e. formalin fixed paraffin embedded-FFPE). A positive control comprises a tissue or cell block containing the biomarker (antigen/DNA/RNA) of interest. Cell lines or purified cells from tissues or blood samples of affected patients are a valuable tool to provide known positive controls. These cells can provide a homogeneous tissue in a desirable amount, and properties can be controlled by molecular, cytogenetic and biochemical characteristics. Cells created in a paraffin block can provide sections for studying ex-vivo cell cycles, signaling pathways, and activation-dependent effects with biochemical agents. Cells grown in culture can be cytospun or prepared as cell smears on glass slides, however, conditions are quite different from tissue blocks which has been fixed, dehydrated and embedded in paraffin.

Cell pellets fixed in formalin become very tough, therefore embedding the pellet into paraffin creates a pellet with very dense cells. It is difficult to create cell blocks that serve as positive controls that are of a uniform density because of the clumping of the cells. And, without uniform density, cell block staining, image scanning and analysis may be inconsistent.

The current invention is to create a "homogeneous" cell block that has superior homogeneity of cells evenly distributed within the section to provide an even distribution of cells which will be used as a control standard.

The lack of reliable controls in IHC/ISH studies is a recognized problem. For example, it was recently noted that ". . . IHC as a platform for biomarkers has been challenged by more quantitative molecular assays with reference standards but that lack morphologic context. For IHC to be considered a "top-tier" biomarker assay, it must provide truly quantitative data on par with non-morphologic assays, which means it needs to be run with reference standards . . . . Until pathologists can run immunohistochemically assays with known controls that serve as true reference standards, the use of MC on histologic sections will be considered a less valued or preliminary method of defining a biomarker" (Dunstan et al, *Toxicologic Pathology*, 39: 988-1002, 2011).

Therefore, there is a need within the medical and research industries to produce reliable controls, such as a cell block of uniformly distributed cells, or ratio of cells, for use as a positive control for a biomarker in immunohistochemistry slide scanning and image analysis.

SUMMARY OF THE INVENTION

The present invention encompasses an in vitro tissue technology method for creating a homogenous mixture cell block for use as a molecular pathology standard and tissue based biomarker standard. The present invention also comprises a solid composition (i.e. cell block) of homogenous cells produced via this method, such as formalin fixed paraffin embedded (FFPE) cells, and a method of use of the composition/block as a control or standard in immunohistochemistry studies.

The present method of making a cell block permits the mixing of different types of cells and/or the same types of cells with a precise mixture/ratio as required for tissue based biomarker standards.

The cell composition/block contains cells in a "homogeneous" state, meaning the cells are distributed evenly within the whole cell block while a minimal number of large clumps are present. The "homogenous" stage also means that a certain defined percentage or number of cells within the composition/block are all evenly distributed. For example, the cell block may contain 50% cell A and 50% cell B, wherein it remains this ratio of homogeneity throughout the whole cell composition/block such that each slice or cross-section of the composition/block will comprise an evenly distributed number of 50% Cell A/50% Cell B ratio. The ratio of cells may be defined with: 1) different types of cells; 2) different combinations of certain designated percentages of each cell type; 3) cells with different treatments (such as of biological process, chemicals, drugs, radiations, and temperature); and, 4) cells with different genetic modifications such as mutations, insertion of a gene, etc. These types of mixture cells are built into the blocks with a certain ratio.

The cell mixture within the composition/block may also comprise the following: a mixture of the same type of cell with different genetic modifications; a mixture of the same type of cell with different protein or nucleic acids expression; and a mixture of different types of cells with different genetic backgrounds, and/or different expression level of genes and/or proteins.

The homogeneous cell composition/block of the present invention further comprises the properties that the block may be scanned while in a fresh stage, cut with any kind of cutting device, and with or without changing its temperature. The cell block can also be processed to formalin fixed paraffin embedded (FFPE) and cut as FFPE section utilizing any cutting device not limited to a rotator microtome, sliding microtome and any other cutting methods. It is noted, though, that other non-FFPE homogenous cell blocks may be produced by the method of the present invention.

The method of use of the homogeneous cell block (i.e. FFPE and non-FFPE) of the present invention is to utilize sections of the cell block as a biomarker standard for any tissue based biomarker studies, as well as biomarker analysis using molecular biology methods such as PCR, sequencing, and microarrays. The FFPE cell section with defined number of cells with defined ratio/mixture percentage is used as a standard for sensitivity and specificity evaluation histology based biomarker studies run using either machines or manual operation methods.

The detection of homogeneity can be performed using cell counting of the same type of cell or different types of cells present in the section. Cell counting methods are well known in the art, such as by digital immunohistochemistry devices (e.g. Aperio ScanoScope). Detection of homogeneity can also be confirmed by the extraction and quantification of nucleic acids from each cell block section to determine the amount of nucleic acids in each block and the ratio of a mixture of cells within the block. Methods of DNA extraction and quantification are well known in the art: PCR, digital PCR and/or sequencing methods.

The method of making the cell composition comprises: pre-treatment of cells for cell block preparation; cell block preparation; sectioning cell blocks and hematoxylin staining; and DNA extraction and quantitation. The density of the cells within the final composition/block is controlled by adjusting the size of the mold in order to produce cell sections of a certain number/density/count, wherein each section contains a particular number of cells within a certain defined limit. This method produces cell blocks of a certain size and length to control the number of cells in each block in order to produce a cell section of a certain number (i.e. pre-designated number), wherein each section contains a particular number of cells within a certain defined limit, or range.

The steps in the method of making the in vitro solid composition (i.e. cell block) comprise: a) passing cells through a cell collection device, wherein said cells are in suspension, fixed pellet, or unfixed pellet form; b) performing cell counting and cell viability; c) fixing the cells in a composition comprising paraformaldehyde in PBS to create a cell pellet; d) preparing the molds; re-suspending the cells in PBS; and immobilizing the suspension in controlled temperature; e) injecting the cell suspension into a mold of predefined size and shape at a controlled temperature; f) cooling and treating the cells with a paraffin processor; and, g) performing DNA extraction and quantification to demonstrate cell block homogeneity.

The cell block preparation step in the method of making the in vitro solid composition (i.e. cell block) comprises: a) passing cells through an apparatus to create a homogenous mixture of immobilized cells; b) injecting the cell mixture into a Mold A (first mold), set, and remove from the Mold A; and, c) processing cell blocks with paraffin, removing individual blocks from paraffin, and embedding into a Mold B (second mold).

Step (a) of the cell block preparation further comprises utilizing an apparatus comprising three vertical layers: 1) an upper cell containing chamber comprising one or more center holes; 2) a middle rotating chamber with a primary hole to pass the cells through, and a secondary hole to inject fluids; and 3) a lower cell collection chamber. The method of use of the apparatus comprises: 1) passing the cells through the upper cell containing chamber onto the rotating primary hole of the middle chamber; 2) then passing the cells through the middle chamber's primary hole, which is of a specific size, while injecting a fluid (i.e. %3 agarose) through a secondary hole; and 3) then collecting the cells in a chamber below the middle chamber.

The primary hole in the middle chamber is of a size in the range of 2 to 4 millimeters. The specific size of the primary hole is determined by the amount of cells in use. The secondary hole in the middle chamber is used to inject 3% agarose of a specific volume while the cells are being passed through the primary hole. The specific volume is determined by the desired final density of cells in the cell block. Passing the cells pellets, especially FFPE, through the apparatus and suspending them using 3% agarose, causes the cells to mix with the fluid and for the suspension to become uniform in cell density, or ratio of cell densities.

BRIEF DESCRIPTION OF DRAWINGS

The in vitro homogenous cell block, methods of making, and methods of use that embody the above and other inventive features will now be described with reference to the following drawings:

FIG. 3 is a table comprising the cell block paraffin processing schedule.

FIG. 4 is a table comprising the Hematoxylin Staining Procedure.

FIG. 5 is a table comprising the DNA yield of different cell blocks of an exemplification utilizing the present method.

DETAILED DESCRIPTION

The following is a method of the present invention to prepare 10 μm FFPE sections of homogenous cell blocks, although it is noted that one of skill in the art would readily know how to adjust this disclosure for producing other types of homogenous cell blocks, such as 5 μm FFPE sections.

Step (120) Comprises the Pre-Treatment of Cells for Cell Block Preparation

1. Remove tissue culture medium and wash cells once with phosphate buffered saline (PBS).
2. Detach cells using trypsin and stop trypsinization by adding culture medium.
3. Centrifuge cells at 800×g for 5 minutes and remove supernatant.
4. Wash cell pellet once with PBS.
5. Re-suspend the cells in 15 ml PBS and place them in the upper chamber of the apparatus of FIG. 2.
6. Pass the cell suspension through a cell strainer in the upper chamber of FIG. 2 (e.g. 70 micrometer).
7. Perform cell counting and cell viability using a Cellometer Auto T4 and Trypan blue staining.

8. Fix the cells for 24 hours at room temperature with freshly prepared 2% paraformaldehyde (PFA) in PBS.
9. After fixation, centrifuge the cells at 800×g for 5 minutes and remove the supernatant.
10. Rinse the cell pellet once with 70% ethanol. Keep at 4° C. until use.

Step (140) Comprises Cell Block Preparation

Cylindrical molds of size (4 mm in radius, 145 mm in length) (MOLD A) are used for making the cell block. The one time use cell block Mold A's (first molds) are kept at −10° C. for one hour before use. The cell pellet is re-suspended in PBS.

Because cell pellets fixed in formalin or paraformaldehyde (PFA) become very tough when the pellets are subsequently embedded into paraffin, they create a pellet with very dense cells. To prevent this, the fixed cell pellet is passed through the apparatus 200 illustrated in FIG. 2, which mixes the cells with the solution simultaneously while it goes through the upper chamber to the middle chamber. Therefore, this makes them into a very even suspension of cells.

Figure 2:
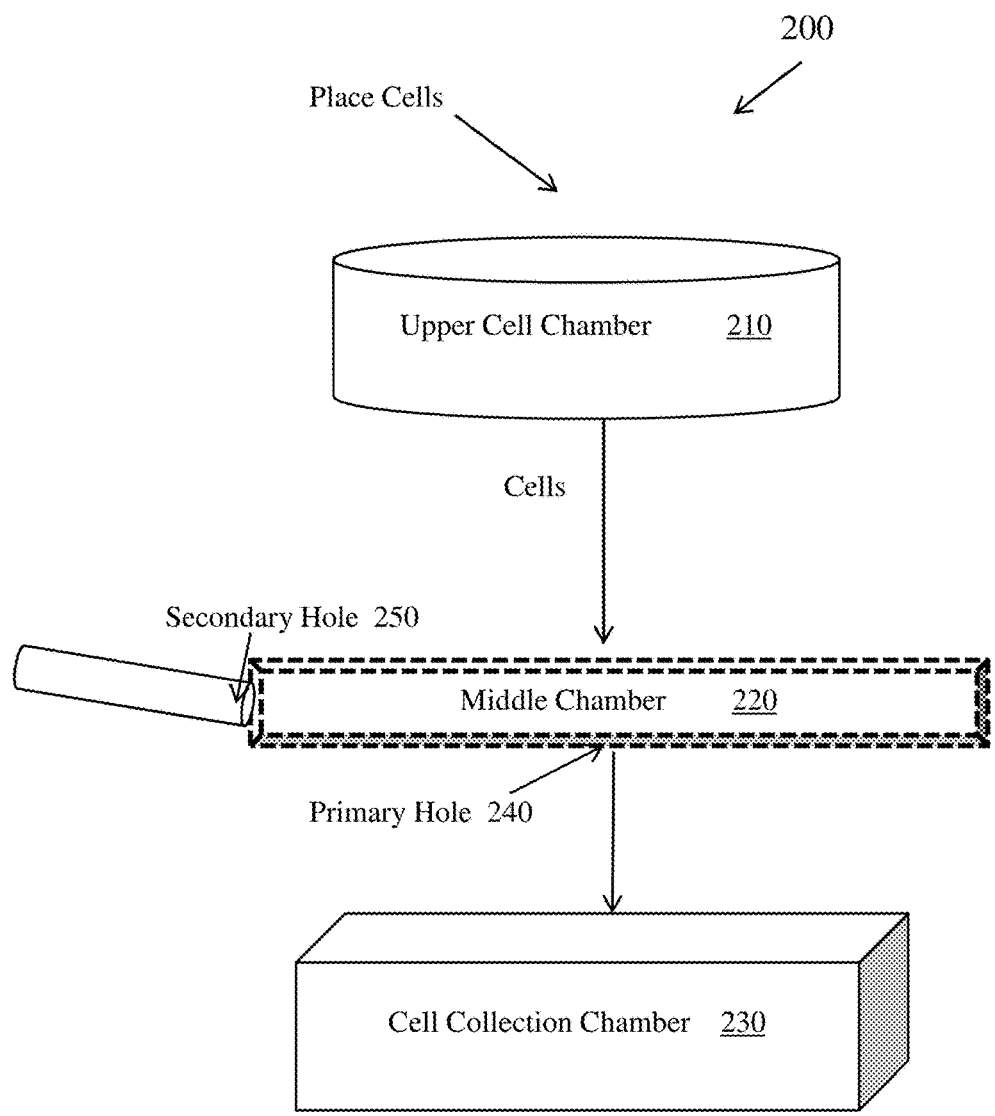
FIG. 2 is an image of an apparatus used in steps of the method of preparing the homogenous cell blocks.

As shown in apparatus 200 of FIG. 2, the re-suspended cells are passed through the upper chamber 210 through the hole in the middle chamber 220. The secondary hole or tube 250 then injects a fluid simultaneously (e.g. 3% agarose) onto the rotating hole to mix with the cells. The cell/agarose mixture then flows through the middle chamber hole 240 onto the lower collection chamber 230.

The cell/agarose mixture is then injected into the Mold A, which is subsequently kept at −10° C. for 5 minutes. The solid composition (i.e. cell block) is then removed from the Mold A and put into individual 50 ml tubes containing 70% ethanol. The cell blocks are processed for paraffin on individual 50 ml tubes using the sequential steps of procedures listed in the table of FIG. 3 comprising the Cell Block Paraffin Processing Schedule.

Immediately after paraffin processing, individual blocks are removed from the paraffin and embedded onto a cubed paraffin Mold B (2 cm*2 cm*2 cm) (second mold). The cell blocks are wrapped with parafilm and kept in air-tight box at 4° C. until sectioning.

Step (160) Comprising Sectioning Cell Blocks and Hematoxylin Staining

The cell blocks from Mold B are removed from the 4° C. refrigerator and mounted onto cassettes for sectioning utilizing a Leica microtome. A single-use high profile microtome blade is used for the sectioning of each cell block; 10 μm FFPE sections are prepared from each block and sections are mounted onto positively charged glass slides and left for air drying at room temperature for 30 minutes. The slides are then baked in a 56° C. oven for 20 minutes before hematoxylin staining using the procedure shown in the table of FIG. 4.

Confirm Cell Block Homogeneity

To confirm homogeneity of the cell blocks, multiple sections (e.g. 1000 cross-sections) are cut from a cell block containing millions of cells, and DNA extraction is performed on selected individual sections (e.g. every 100th section) as per step 180, and the DNA is quantified as per step 200. Additionally, digital microscopy images taken of hematoxylin-stained cell sections show the cells scattered evenly within the cell block section.

Step (180) Comprises DNA Extraction from 10 μm FFPE Cell Block Section

DNA extraction methods are well known in the art. By way of exemplification, DNA extraction may be performed using the Qiagen DNeasy Blood & Tissue Kit (cat. #69504, Qiagen, USA) according to the manufacturer's protocol with two exceptions: 1) Proteinase K digestion is performed overnight in a 56° C. water bath; and, 2) DNA is eluted with 100 μl elution buffer twice to yield a total volume of 200 μl DNA.

Step (200) Comprises DNA Quantitation Using PicoGreen Fluorescent Dye

Likewise, DNA quantification methods are well known in the art. By way of exemplification, the DNA is quantified using a Quant-iT PicoGreen dsDNA Reagent and Kit (Molecular Probes, Eugene, Oreg.). Standard curve samples are freshly diluted from the Lambda DNA standard before each batch of sample measurements. DNA measurement of unknown samples are performed according to the manufacturer's recommendation. Fluorescence readings are taken with a TBS-380 Mini-Fluorometer (Turner Biosystems, Sunnyvale, Calif.) using 10×10 mm square polystyrene disposable cuvettes. Sample DNA concentrations are then extrapolated from the Lambda DNA standard curve.

EXEMPLIFICATION

Figure 1:
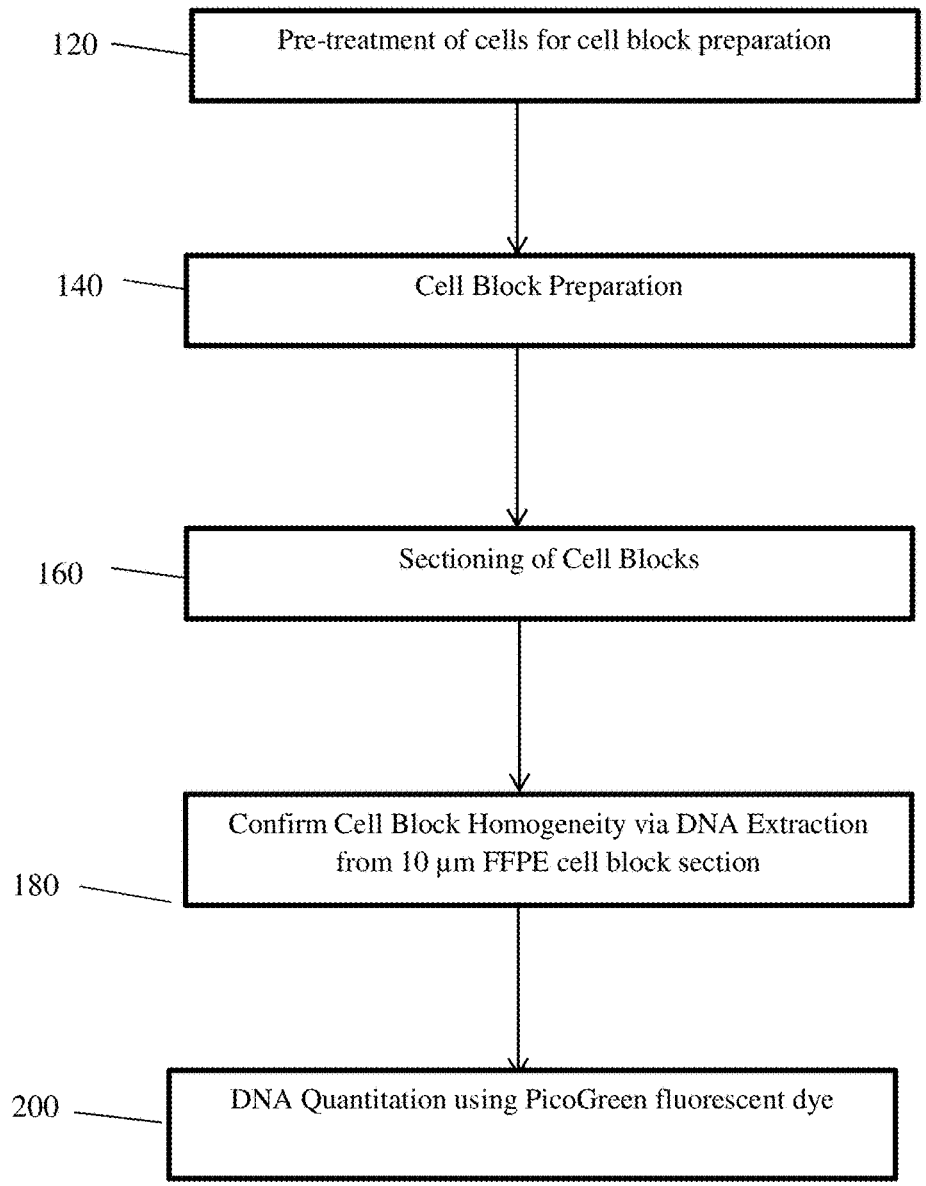
FIG. 1 is a flowchart of steps for preparing in vitro homogenous cell blocks.

An in vitro homogenous cell block comprising HCT-116 cells, wherein the block is produced by the method of the present invention as disclosed in FIGS. 1 & 2, was quantified for the amount of DNA yield in a 10 micrometer thick slice of the block. The results are shown in the table of FIG. 5 disclosing: the cell block initial number of cells (20, 40, 80 and 160 million); the cell number per 10 micrometer section from 1200 sections total (11,650; 23,889; 61,170; and 126,500) respectively; and the DNA yield per the corresponding 10 micrometer section (62, 131, 245, and 512).

Figure 6:
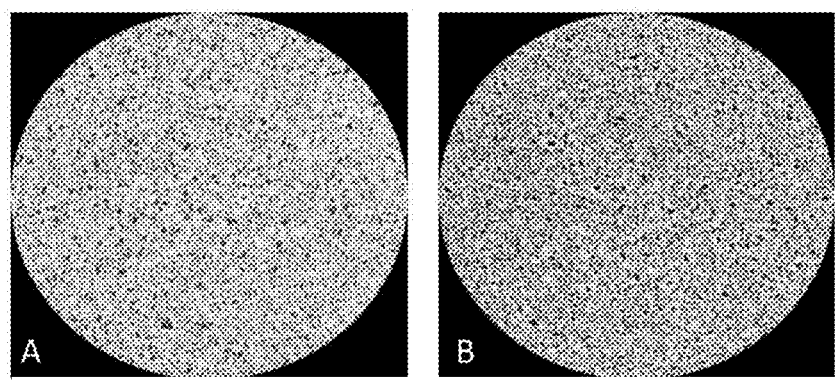
FIG. 6 illustrates images of the exemplification of FIG. 5 demonstrating the homogenous nature of the cell distribution.

Images generated using Aperio ScanScope whole slide scanner of the above hematoxylin stained blocks of cells of 40 million (Section A) and 80 million (Section B) demonstrate the homogenous nature of the cells blocks (See FIG. 6). Nuclear cell count on hematoxylin positive cell section was performed using Aperio ImagesScope program. The left image (Section A) shows 23,000+ cells; and the right image (Section B) shows 61,000+ cells, both of which comprise the cells evenly distributed throughout the section.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A positive control experimental standard comprising a solid composition, wherein the solid composition comprises a homogenous mixture of cells within a formalin fixed paraffin embedded block, wherein the cells are evenly distributed throughout the solid block's volume with a uniform distribution and density of non-clumped cells of a same cell type, or of a ratio of different cell types, within the mixture of cells of a pre-determined number of each cell type, produced by the steps comprising,
   a. passing a plurality of pre-treated cells vertically through holes in a multi-chambered-tiered apparatus and mixing the pre-treated cells with a fluid simultaneously to create a homogenous cell mixture of immobilized cells, wherein the multi-chambered-tiered apparatus comprises,
      a circular upper cell containing chamber (FIG. 2, item 210) able to pass the pre-treated cells onto a circular rotating middle secondary chamber (FIG. 2, item 220);
      a circular rotating middle secondary chamber (FIG. 2, item 220) with a centered primary hole (FIG. 2, item 240) that is adjustable in diameter and able to pass the pre-treated cells of a pre-determined amount through to a lower cell collection chamber (FIG. 2, item 230), and a suspended secondary hole or an open-ended tube (FIG. 2, item 250) able to simultaneously inject the fluid to create a homogenous cell mixture, wherein the suspended secondary hole, or the open-ended tube, is positioned between said upper chamber and said lower chamber, and is able to inject liquid into the circular rotating middle secondary chamber;
      a lower cell collection chamber (FIG. 2, item 230) positioned to receive the homogenous cell mixture from the rotating middle secondary chamber;
   b. injecting the homogenous cell mixture into a first mold, letting the mixture set to immobilize the cell mixture, and removing a solid composition from the first mold;
   c. processing the solid composition with paraffin, removing the solid composition from the paraffin, and embedding the solid composition into a second mold to produce a formalin fixed paraffin embedded (FFPE) cells; and,
   d. removing the solid composition from the second mold, wherein said solid composition comprises a homogenous mixture of formalin fixed paraffin embedded (FFPE) cells with a uniform density of cells throughout said solid composition.

2. The positive control experimental standard of claim 1, wherein said mixture of FFPE cells comprises a ratio of: a different types of cells; a different combination of certain percentages of each cell type; and/or a same type of cells exposed to different treatment protocols; and, wherein the ratio of the mixture of cells is evenly distributed with a uniform density within said solid composition, and without or with minimal large cell clumping.

3. The positive control experimental standard of claim 1, wherein the mixture of cells within said solid composition comprises a ratio of: a same type of cells with different genetic modifications; a same type of cells with different protein or nucleic acids expression; a different types of cells with different genetic backgrounds; and/or, different types of cells with different gene/protein expression levels; and, wherein the ratio of the mixture of cells is evenly distributed within said solid composition.

4. The positive control experimental standard of claim 1, wherein the liquid injected comprises agarose.

5. The positive control experimental standard of claim 4, wherein said liquid comprises 3% agarose.

6. The positive control experimental standard of claim 4, wherein the pre-treated cells passed through said apparatus are in suspension, a fixed pellet, or an unfixed pellet form.

7. The positive control experimental standard of claim 1, wherein pre-treating cells comprises the steps of, fixing the cells in paraformaldehyde or formaldehyde and phosphate buffered saline (PBS), then centrifuging and rinsing the cells.

8. The positive control experimental standard of claim 7, wherein the pre-treatment of cells further comprises:
   a) fixing the cells for 24 hours at room temperature with freshly prepared 2% paraformaldehyde in PBS to create a cell pellet;
   b) centrifuging the cell pellet;
   c) rinsing the cell pellet with 70% ethanol; and,
   d) storing the cells at 4 degrees Celsius.

9. The positive control experimental standard of claim 1, which is quality controlled, wherein the quality control comprises sectioning the solid composition of claim 1 into 10 μm sections, baking at 56 degrees Celsius for 20 minutes, and staining with hematoxylin.

10. The positive control experimental standard of claim 9, comprising subjecting multiple sections of claim 9 to DNA extraction and DNA quantification to verify the mixture FFPE cells in said block are homogenous.

* * * * *